United States Patent [19]

Lee et al.

[11] Patent Number: 5,637,352

[45] Date of Patent: Jun. 10, 1997

[54] PREPARATION METHOD FOR LEAD-TITANIUM BASED THIN FILM

[75] Inventors: Wan-in Lee; Jun-ki Lee, both of Kyungki-do, Rep. of Korea; Seshu B. Desu, Blacksburg, Va.

[73] Assignee: Samsung Electronics Co., Ltd., Suwon-Kyungki-Do, Rep. of Korea

[21] Appl. No.: 539,518

[22] Filed: Oct. 5, 1995

[30] Foreign Application Priority Data

Oct. 10, 1994 [KR] Rep. of Korea ............... 1994 25903
Nov. 25, 1994 [KR] Rep. of Korea ............... 1994 31300

[51] Int. Cl.$^6$ ........................................... C23C 16/40
[52] U.S. Cl. ............................... 427/255.3; 427/248.1
[58] Field of Search ........................... 427/100, 226, 427/248.1, 255.3, 576

[56] References Cited

U.S. PATENT DOCUMENTS 5,139,999 8/1992 Gordon et al. ........................... 505/1
5,372,850 12/1994 Uchikawa et al. .................. 427/255.3
5,431,958 7/1995 Desu et al. ........................... 427/255.3

*Primary Examiner*—Shrive Beck
*Assistant Examiner*—Timothy H. Meeks
*Attorney, Agent, or Firm*—Seidel, Gonda, Lavorgna & Monaco, PC

[57] ABSTRACT

An organometallic lead precursor, represented by following formula:

$$L_xPb(THD)_2 \qquad [I]$$

wherein L is an electron donor ligand selected from the group consisting of $NR_3$ (R=H, $CH_3$) gas and $Cl_2$ gas; THD denotes 2,2',6,6'-tetramethyl-3,5-heptanedione; and x is in the range of 0.5 to 2, is prepared by flowing a gas phase electron donor into a bubbler containing bis (2,2',6,6'-tetramethyl-3,5-heptanedione)Pb at a predetermined temperature, to synthesize, in-situ, an adduct. The precursor exhibits a remarkable improvement in volatility, and in stability at the vaporization point.

Lead-titanium based thin films prepared from the precursor, display superior reproducibility and reliability.

6 Claims, 3 Drawing Sheets

PREPARATION METHOD FOR LEAD-TITANIUM BASED THIN FILM

BACKGROUND OF THE INVENTION

1. Field of the invention

The present invention relates, in general, to a novel organometallic lead precursor and its in-situ synthesis and, more particularly, to an organometallic lead precursor with an improvement in volatility. Also, the present invention is concerned with a lead-titanium based thin film using the same and with a preparation method for preparing the same.

2. Description of the Prior Art

PbTiO$_3$ thin film or its related thin films (hereinafter referred to as "PT thin films"), used as ferroelectric thin films for semiconductor capacitors, are prepared from organometallic precursors. For production of the PT based thin films, there is generally used a metal-organic chemical vapor deposition process (hereinafter referred to as "MOCVD"), a technique for growing thin layers of compound semiconductors. In practice, MOCVD comprises preheating a liquid or solid of organometallic precursor to vaporize it and decomposing the vapor by heat or plasma, to deposit a thin film.

It is necessarily required that appropriate organometallic precursors be selected in order to obtain desired properties and quality of the PT based thin film. The following are the general conditions that organometallic precursors should have: first, organometallic precursors should be able to be easily vaporized and deposited at low preheat temperatures, in addition to being stable at the preheat temperatures; second, the difference between the vaporization temperature and the decomposition temperature should be large enough; third, it is preferred that the organometallic precursors are not decomposed or changed by the moisture contained in air; finally, they should not be environmentally toxic.

Among the organometallic precursors useful for preparing the PT based thin films, representative are organometallic Ti precursors and organometallic Pb precursors. The former has extensively been researched and developed by virtue of its ability to vaporize at relatively low temperatures. On the other hand, most of the organometallic lead precursors have problems in that they are extremely harmful to human body, and have poor in thermal stability.

Bis(2,2',6,6'-tetramethyl-3,5-heptanedione)Pb (hereinafter referred to as "Pb(THD)$_2$"), an organometallic lead precursor, exhibits encouraging characteristics, such as low toxicity and high moisture stability. It is thus, most widely used. However, this organometallic lead precursor shows a crucial problem in that the difference between its vaporization temperature and decomposition temperature is not large. That is to say, Pb(THD)$_2$ is thermally instable at around 150° C., a typical temperature at which solid Pb(THD)$_2$ overcomes its intermolecular interaction and is vaporized.

Referring to FIG. 1, Pb(THD)$_2$ isotherms show weight loss with the lapse of time. A TGA balance is utilized for measuring the weight loss. At temperatures lower than 120° C., the weight of Pb(THD)$_2$ decreases steadily. However, at temperatures higher than 120° C., the weight decrease is not observed after a certain time interval. It is believed that Pb(THD)$_2$ is thermally stable only up to 120° C., and thermally instable above 120° C. such that it decomposes forms and/or a nonvolatile chemical species.

As described previously, a temperature of 140° to 160° C. is required to vaporize Pb(THD)$_2$ to the degree that it is applicable to MOCVD, but vaporization and decomposition of Pb(THD)$_2$ occurs simultaneously at 130° C. or more. In practice, when Pb(THD)$_2$ is used to deposit PT based thin films, decomposition of the precursor occurs the in bubbler and the bubbler must be charged with fresh precursor after several runs. Accordingly, it is virtually impossible to prepare a thin film with Pb(THD)$_2$, in a large quantity and in uniform quality. Consequently, despite low toxicity and high moisture stability, Pb(THD)$_2$ has great difficulties in its application to Pb MO(metal organic) sources because of its low volatility and poor thermal stability.

SUMMARY OF THE INVENTION

Therefore, a primary object of the present invention is to overcome the above problems encountered in prior art and to provide a novel organometallic lead precursor, improved in volatility and in stability at its vaporizing point.

It is another object of the present invention to provide a method for synthesizing the organometallic lead precursor by a in-situ process.

It is a further object of the present invention to provide a lead-titanium thin film made of an organometallic lead precursor, which is superior in reliability and reproducibility.

Based on intensive and through research and study by the present inventors, the above objects are accomplished by providing an organometallic lead precursor for ferroelectric lead, titanium based thin film, represented by the following Formula I:

$$L_x Pb(THD)_2 \qquad \text{[I]}$$

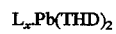

wherein L is an electron donor ligand selected from the group consisting of NH$_3$, N(CH$_3$)$_3$, and Cl$_2$ gas; THD denotes 2,2',6,6'-tetramethyl-3,5-heptanedione; and x is in the range of 0.5 to 2.

In accordance with another aspect of the invention, there is provided a method for the preparation of organometallic lead precursor, comprising flowing an electron donor in gas phase into a bubbler containing bis(2,2',6,6'-tetramethyl-3, 5-heptanedione)Pb at a predetermined temperature, to synthesize, in-situ, an adduct represented by the above formula.

In accordance with a further aspect of the invention, there is provided a method for the deposition of lead-titanium based thin film, comprising the steps of: flowing an electron donor in the gas phase into a bubbler containing bis(2,2',6, 6'-tetramethyl-3,5-heptanedione)Pb at a selected reaction temperature, to synthesize, in-situ, an adduct represented by the above formula; cooling the adduct to solidify it; heating the bubbler to a temperature lower than said reaction temperature, to volatilize the adduct; passing the adduct with a carrier gas into a metal-oxide vapor deposition reactor; and reacting the volatilized adduct with a titanium precursor source at a high temperature and at reduced pressure in an oxidative atmosphere by metal-organic chemical vapor deposition.

BRIEF DESCRIPTION OF THE DRAWINGS

The above objects and other advantages of the present invention will become more apparent by describing in detail the preferred embodiment of the present invention with reference to the attached drawings in which.

DETAILED DESCRIPTION OF THE INVENTION

Figure 1:
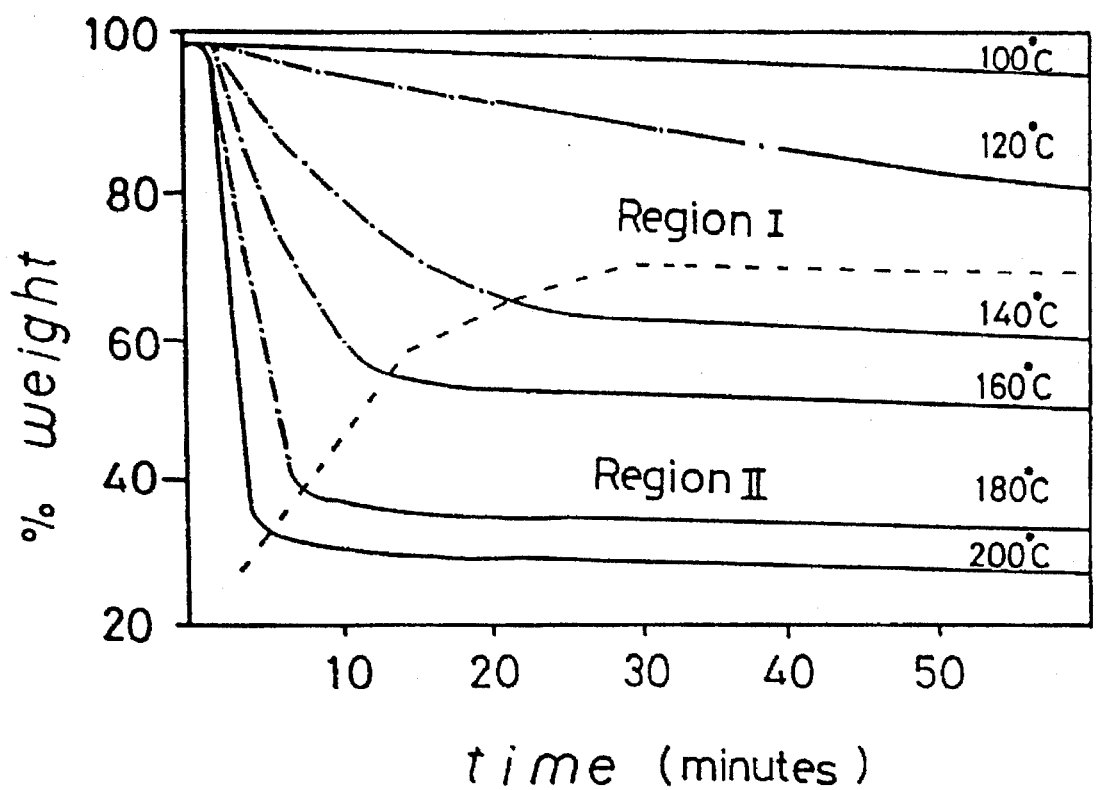
FIG. 1 shows Pb(THD)$_2$ isotherms illustrating weight loss with the lapse of time.

In a Pb(THD)$_2$ molecule, Pb(II), the central atom, is coordinately bonded with THD, the ligands, by incorporation of the electrons on the carbonyl groups of the ligands into the bonding sphere of the metal. Generally, THD, which is a neutral ligand without nominal charge, cannot donate sufficient electrons to the Pb atom. Accordingly, the electrophilic Pb atom comes to attractively interact with the THD ligands of neighboring Pb(THD)$_2$ molecules. As a result, Pb(THD)$_2$ molecules form a stable solid structure at room temperature.

On the other hand, coordination bonding of the Pb atom with additional ligands capable of donating sufficient electrons results in weakening or breaking the intermolecular interaction in the solid structure. The coordinated Pb(THD)$_2$ molecules are able to volatilize at lower temperatures than original Pb(THD)$_2$.

In accordance with the present invention, NH$_3$, N(CH$_3$)$_3$, or Cl$_2$ molecules are utilized as the additional electron donor. Since the NH$_3$ or Cl$_2$ molecule has lone electron pairs, it can supply sufficient electrons to the metal atom. In addition, such an additional electron donor is relatively small in size, so that it can easily contact with the Pb atom. Therefore, the NH$_3$, N(CH$_3$)$_3$, or Cl$_2$ electron donor itself can be chemically adducted to Pb(THD)$_2$, as represented by the following reaction formulas:

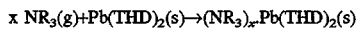

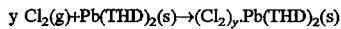

wherein R is H or CH$_3$; x is in the range of 0.5 to 2; and y is in the range of 0.5 to 2. In the NH$_3$, N(CH$_3$)$_3$, or Cl$_2$ adduct, the additional electron donors break the intermolecular interaction among Pb(THD)$_2$ molecules, so that the adduct can be volatilized at low temperatures. The obtained adduct can be utilized as an organometallic lead precursor with a remarkable improvement in volatility.

In accordance with the present invention, the organometallic lead precursor is prepared by a method comprising flowing a gas phase electron donor into a bubbler containing Pb(THD)$_2$ at a predetermined temperature, to synthesize, in-situ, an adduct represented by the following formula:

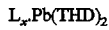

wherein

L is an electron donor ligand selected from a group consisting of NH$_3$, N(CH$_3$)$_3$, and Cl$_2$; and x is in the range of 0.5 to 2.

The gas phase electron donor used to prepare the organometallic lead precursors of the present invention is selected from the group consisting of NH$_3$, N(CH$_3$)$_3$, and Cl$_2$.

A more detailed description for the preparation of the present organometallic lead precursors will be given as follows.

For the preparation of (NR$_3$)$_x$.Pb(THD)$_2$ (R=H or CH$_3$) by an in-situ process, solid phase Pb(THD)$_2$ is placed in a bubbler, and NR$_3$ (R=H or CH$_3$) gases are used as a carrier gas. The temperature of the bubbler is kept to 100° to 120° C. Pb(THD)$_2$ in the bubbler reacts with NR$_3$ (R=H or CH$_3$) carrier gas, and (NR$_3$)$_x$.Pb(THD)$_2$ (R=H or CH$_3$, 0.5≦x≦2) is synthesized. The produced chemical species are so volatile that they are vaporized instantly at the bubbler temperature of 100° to 120° C. Vaporized (NR$_3$)$_x$.Pb(THD)$_2$ is carried by unreacted electron donor gases (NH$_3$ or N(CH$_3$)$_3$), and can be used for the thin film deposition in the reactor. Consequently, by simply flowing NR$_3$ (R=H or CH$_3$) as carrier gas, Pb(THD)$_2$ precursor can be easily vaporized at a temperature of 100° to 120° C. This bubbling temperature is about 40 degrees lower than that of conventional processes (using Pb(THD)$_2$ as precursor and Ar or N$_2$ as carrier gas). Therefore, there is no decomposition of precursor during the bubbling process and a constant vapor pressure can be maintained over an elapsed bubbling time. (NR$_3$)$_x$.Pb(THD)$_2$ synthesized by the in-situ process was analyzed by an Element Analysis Technique. It was ascertained that the value of x is 0.5~2.

Figure 2:
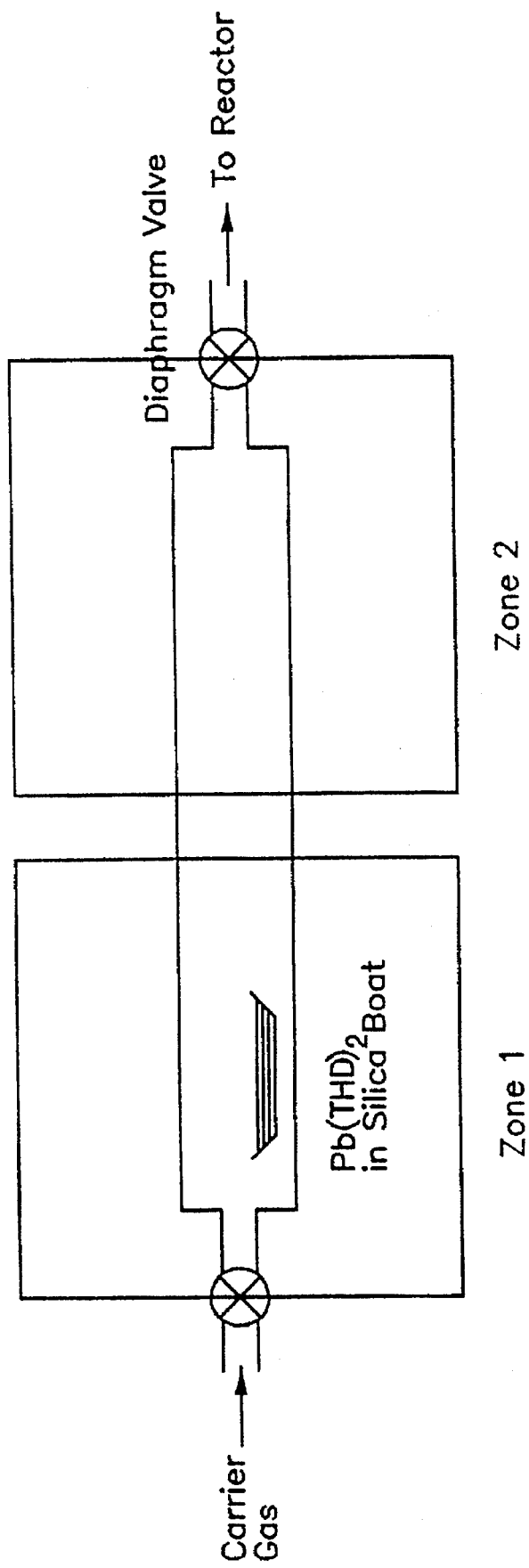
FIG. 2 is a schematic longitudinal section showing bubbler equipment useful to synthesize an organometallic lead precursor of the present invention by an in-situ process.

For preparation of (Cl$_{12}$)$_x$.Pb(THD)$_2$, Pb(THD)$_2$ of solid phase is placed in the silica boat as shown in FIG. 2 and then, an electron donor in the gas phase (Cl$_2$) is supplied under the control of a Mass Flow controller. At an elevated temperature, an adduct between Pb(THD)$_2$ and Cl$_2$ is synthesized in the gas phase. As for the reaction conditions, where Cl$_2$ gas flows through the tube, the temperature of Zone 1 is maintained in the range of about 130° to about 150° C. At this temperature range, Cl$_2$ gas reacts with Pb(THD)$_2$ rapidly. Thereafter, the synthesized gas phase adduct ((Cl$_2$)$_x$.Pb(THD)$_2$) is solidified in Zone 2 because the wall of the tube in Zone 2 is cooled to room temperature. Since Cl$_2$ gases are instantly reacted with Pb(THD)$_2$ under these conditions, the amount of synthesized adduct can be calculated on the basis of the amount of charged Pb(THD)$_2$ in Zone 1. Meanwhile, unreacted electron donor gas is not passed into a reactor connected to the tube of Zone 2, but drained through a bypass and removed through reaction with an aqueous NaOH solution. Then, the carrier gas is replaced with N$_2$ and the bubbler temperature is adjusted to 80° to 110° C., which is 40 to 80 degrees lower than the temperature of the conventional process.

Figure 3:
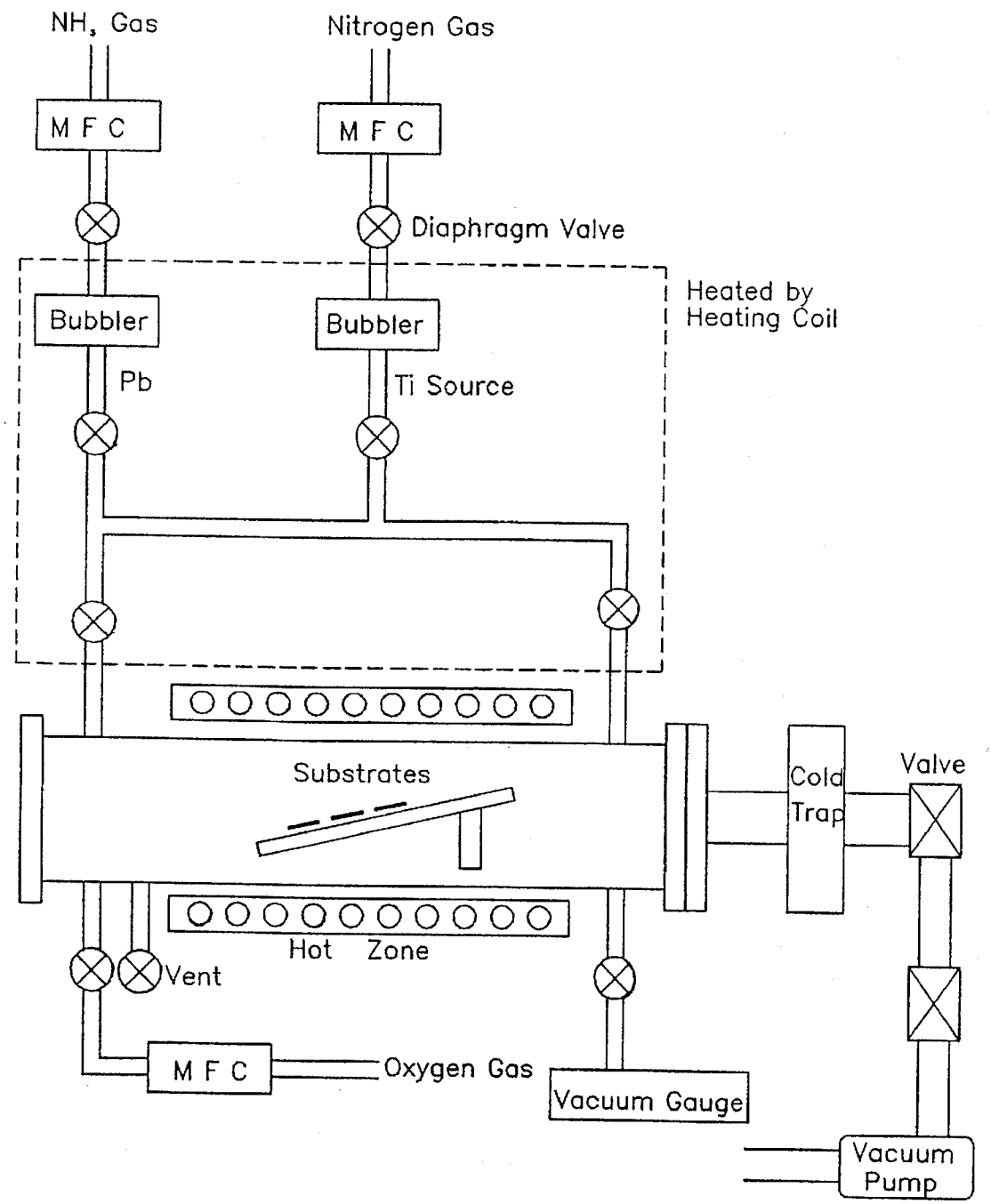
FIG. 3 is a schematic view showing an MOCVD apparatus useful for preparing a lead-titanium based thin film from the organometallic lead precursor of the present invention.

Referring now to FIG. 3, there is shown an MOCVD apparatus useful to deposit PT based thin films. As shown in this figure, this MOCVD apparatus, which is a kind of a vacuum CVD apparatus operating in a hot wall manner, is provided with bubbler equipment for precursor sources, e.g. a Pb source and a Ti source; a reactor; and a cold trap.

For the deposition of a PT based thin film by using NR$_3$ (R=H, CH$_3$) adducted Pb(THD)$_2$, Pb(THD)$_2$ is first charged into a bubbler. Then, the temperature of bubbler is adjusted to 100°~120° C. and NR$_3$gas with a flow rate of 50~100 sccm is employed. The in-situ generated (NR$_3$)$_x$.Pb(THD)$_2$ is carried to a reactor by the NR$_3$, which is not consumed in the reaction with Pb(THD)$_2$. For the Ti source, Ti(O—CH$_2$CH$_3$)$_4$ (hereinafter referred to as "Ti(OEt)$_4$") is typically used, and it is heated to 100°~125° C., while N$_2$ gas is preferably used as a carrier gas.

For the deposition of a PT based thin film by using chlorine-adducted Pb(THD)$_2$, the prepared (Cl$_2$)$_x$.Pb(THD)$_2$ in Zone 2 of the bubbler of FIG. 2 is first heated to 80°~110° C. In order to carry the vaporized chlorine-adducted Pb(THD)$_2$, N$_2$ gas with a flow rate of 50~100 sccm is employed. In the same way, Ti(OEt)$_4$ is used as a Ti source, and 10~20 sccm of N$_2$ gas can be used as a carrier gas. Thereafter, the vaporized precursor sources are decomposed in the reactor heated to a high temperature, for example, about 600° to about 700° C. and then, reacted with oxygen gas which is provided from another regulated route, for deposition of PT based thin film on a substrate. For PbTiO$_3$ thin film, the oxygen gas is flowed in a rate of 500 sccm. The cold trap which is connected with the reactor, in the meanwhile, removes unreacted precursor sources. A vacuum pump works to maintain a reduced pressure in the reactor.

The preferred embodiments of the present invention will now be further described with reference to specific examples.

EXAMPLE 1

The MOCVD apparatus of FIG. 3 was used to deposit a PbTiO$_3$ thin film. 1.0 g of Pb(THD)$_2$ was charged in a stainless tube of the bubbler and heated to about 110° C. Separately, 10 g of Ti(OEt)$_4$ was charged in another bubbler and heated to about 115° C. The Ti source was supplied to the reactor by a carrier gas of N$_2$ with a flow rate of about 15 sccm, whereas the Pb source was supplied by a carrier gas of NH$_3$ with a flow rate of 50 sccm. Then, the reactor was heated to about 600° C., to deposit the PbTiO$_3$ thin film.

More detailed reaction conditions are reported in the following Table I.

TABLE I

Deposition Conditions for PbTiO$_3$

| Item | Reaction Condition | |
|---|---|---|
| | Pb source | Ti source |
| Precursor | Pb(THD)$_2$ | Ti(OEt)$_4$ |
| Temp. in Bubbler | 110° C. | 115° C. |
| Carrier Gas | NH$_3$ | N$_2$ |
| Flow Rate of Carrier Gas | 50 sccm | 15 sccm |
| Oxygen Flow Rate | 500 sccm | |
| Temp. & Pressure in Reactor | 600° C., 2.0 torr | |

Under the conditions given in Table I, the reactor was operated for 30 minutes, to obtain a PbTiO$_3$ thin film of perovskite phase with a thickness of 300 nm.

EXAMPLE II (Cl$_2$)$_x$.Pb(THD)$_2$ was prepared using the bubbler equipment of FIG. 2. For this, a quartz boat containing 1.5 g of Pb(THD)$_2$ was positioned in Zone 1. Zone 1 was heated to 140° C. and Zone 2 was maintained in room temperature by circulating cold water around Zone 2. Dry chlorine gas flowed in a rate of 50 sccm for 20 minutes and was consumed by reaction with Pb(THD)$_2$ positioned in Zone 1. The gas phase adduct thus produced, (Cl$_2$)$_x$.Pb(THD)$_2$, was solidified in Zone 2, cold region.

Thereafter, Example 1 was repeated using the deposition conditions given in the following Table II. Particularly, the carrier gas for the Pb source was replaced by nitrogen gas in this Example.

TABLE II

Deposition Conditions for PbTiO$_3$

| Item | Reaction Condition | |
|---|---|---|
| | Pb source | Ti source |
| Precursor | Cl$_x$.Pb(THD)$_2$ | Ti(OEt)$_4$ |
| Temp. in Bubbler | 95° C. | 115° C. |
| Carrier Gas | N$_2$ | N$_2$ |
| Flow Rate of Carrier Gas | 50 sccm | 15 sccm |
| Oxygen Flow Rate | 500 sccm | |
| Temp. & Pressure in Reactor | 600° C., 2.0 torr | |

Under such conditions, the reactor was operated for 30 minutes, to obtain a PbTiO$_3$ thin film of perovskite phase with a thickness of 350 nm.

Although the Examples illustrate the practice of the present invention using the organometallic lead precursors (NR$_3$)$_x$.Pb(THD)$_2$ where R is H or CH$_3$ and (Cl$_2$)$_x$.Pb(THD)$_2$, for deposition of PbTiO$_3$ thin film, these precursors are believed to provide similar results when other PT based thin films are prepared therefrom.

The following are the advantages obtained when the organometallic lead precursors of the present invention, (NR$_3$)$_x$.Pb(THD)$_2$ and (Cl$_2$)$_x$.Pb(THD)$_2$, are used for PT based thin films.

First, the above precursors can be used repetitively in a bubbler without any decomposition. So, it is possible to obtain a PT based thin film superior in reliability and reproducibility.

Second, the precursors of the present invention are able to be vaporized at much lower temperatures than is Pb(THD)$_2$.

Third, the precursors of the present invention are very stable at the preheat temperatures for vaporization.

Fourth, since (NH$_3$)$_x$.Pb(THD)$_2$ and (Cl$_2$)$_x$.Pb(THD)$_2$ are hygroscopic, there is a danger that these precursors decompose during treatment if they are prepared outside the bubbler and then delivered into the bubbler. In the present invention, the above danger is eliminated because the precursors are synthesized in the bubbler in-situ.

Finally, N$_2$ gas, which is utilized as a carrier gas for (Cl$_2$)$_x$.Pb(THD)$_2$ precursor, prevents corrosion or damage to the reactor.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed herein.

The expression "PT based thin film" or "lead-titanium based thin film", as used in the specification denotes PbTiO$_3$, Pb(ZrTi)O$_3$ (PZT) and doped pb(ZrTi)O$_3$ (PZT), such as Pb(NbZrTi)O$_3$ (PNZT), Pb(LaZrTi)O$_3$ (PLZT), Pb(TaZrTi)O$_3$ (PTZT) and Pb(ScZrTi)O$_3$ (PSZT).

What is claimed is:

1. A method for the deposition of lead-titanium based thin film comprising the steps of:

flowing a gas phase electron donor into a bubbler containing bis (2,2', 6,6'-tetramethyl-3,5-heptanedione)Pb at a selected reaction temperature, to synthesize; in-situ, a gas phase adduct represented by the following formula III:

$$L_x.Pb(THD)_2 \qquad [III]$$

wherein

L is an electron donor ligand selected from the group consisting of NR$_3$, wherein R is hydrogen or methyl, and Cl$_2$;

THD denotes 2,2', 6,6'-tetramethyl-3,5-heptanedione; and x is in the range of 0.5 to 2.0, cooling the adduct to solidify it;

heating the bubbler to a temperature lower than said selected reaction temperature, to volatilize the adduct;

passing the adduct with a carrier gas into a metal-oxide vapor deposition reactor: and reacting the volatized adduct with a titanium precursor source in an oxidative atmosphere to achieve vapor deposition of a lead-titanium based thin film.

2. A method in accordance with claim 1, wherein L is $Cl_2$ and said selected reaction temperature is in the range of from about 130° to about 150° C.

3. A method in accordance with claim 1, wherein L is $C_1$, and said adduct is volatilized at a temperature of about 80° to about 110° C.

4. A method in accordance with claim 1, wherein said adduct is reacted with said titanium precursor source at a temperature of about 600° to about 700° C.

5. A method in accordance with claim 1, wherein said carrier gas is $NR_3$ when L is $NR_3$, where R is hydrogen or methyl.

6. A method in accordance with claim 1, wherein said carrier gas is $N_2$ when L is $Cl_2$.

* * * * *